(12) United States Patent
Fan et al.

(10) Patent No.: US 9,581,560 B2
(45) Date of Patent: Feb. 28, 2017

(54) MULTIPLE-EXCITATION MULTIPLE-RECEIVING (MEMR) CAPACITANCE TOMOGRAPHY

(71) Applicants: The University of Connecticut, Farmington, CT (US); United Technologies Corporation, Hartford, CT (US)

(72) Inventors: Zhaoyan Fan, Willimantic, CT (US); Robert X. Gao, Manchester, CT (US); Jeffery A. Lovett, Tolland, CT (US); Lance L. Smith, West Hartford, CT (US)

(73) Assignees: The University of Conneticut, Farmington, CT (US); United Technologies Corporation, Hartford, CT (US)

( * ) Notice: Subject to any disclaimer, the term of this patent is extended or adjusted under 35 U.S.C. 154(b) by 3 days.

(21) Appl. No.: 14/813,925

(22) Filed: Jul. 30, 2015

(65) Prior Publication Data

US 2015/0338364 A1    Nov. 26, 2015

Related U.S. Application Data

(63) Continuation of application No. 14/024,149, filed on Sep. 11, 2013, now Pat. No. 9,170,224.

(51) Int. Cl.
| | | |
|---|---|---|
| *G01R 27/26* | (2006.01) | |
| *G01N 27/02* | (2006.01) | |
| *G01N 27/22* | (2006.01) | |
| *A61B 5/053* | (2006.01) | |

(52) U.S. Cl.
CPC ......... *G01N 27/026* (2013.01); *A61B 5/0536* (2013.01); *G01N 27/22* (2013.01); *G01N 27/221* (2013.01); *G01R 27/2605* (2013.01)

(58) Field of Classification Search
CPC .... G01N 27/026; G01N 27/221; G01N 27/22; G01R 27/2605; A61B 5/0536
USPC ................................................ 324/658, 674
See application file for complete search history.

(56) References Cited

U.S. PATENT DOCUMENTS

| | | | |
|---|---|---|---|
| 5,919,142 A | 7/1999 | Boone et al. | |
| 7,847,565 B2 | 12/2010 | Woo et al. | |
| 8,508,238 B2 | 8/2013 | Mahalingam et al. | |
| 8,892,198 B2 | 11/2014 | Bohorquez et al. | |
| 2004/0242989 A1* | 12/2004 | Zhu | A61B 5/0536 600/407 |
| 2007/0133746 A1 | 6/2007 | Ortiz Aleman et al. | |
| 2010/0303321 A1 | 12/2010 | McEwan et al. | |
| 2010/0332170 A1 | 12/2010 | Gao et al. | |

(Continued)

*Primary Examiner* — Amy He
(74) *Attorney, Agent, or Firm* — Carlson, Gaskey & Olds, P.C.

(57) ABSTRACT

A method for operating a sensor, including simultaneously exciting a first set of electrodes and sensing an output of each electrode of a second set of electrodes, storing output data corresponding to the output of each electrode of the second set of electrodes in a memory storage device, shifting at least one electrode from the first set of electrodes to the second set of electrodes and at least one electrode from the second set of electrodes to the first set of electrodes, and repeating the simultaneously exciting and sensing, the storing, and the shifting until an output data has been stored for each possible pair of electrodes in the first and second set of electrodes.

10 Claims, 6 Drawing Sheets

(56) References Cited

U.S. PATENT DOCUMENTS

2013/0002264 A1* 1/2013 Garber ................... A61B 5/08
　　　　　　　　　　　　　　　　　　　　　　324/600
2013/0049770 A1　2/2013 Basu et al.

* cited by examiner

MULTIPLE-EXCITATION MULTIPLE-RECEIVING (MEMR) CAPACITANCE TOMOGRAPHY

PRIORITY STATEMENT

This disclosure claims priority to U.S. Provisional Application No. 61/720,538, which was filed on Oct. 31, 2012 and is hereby incorporated by reference herein in its entirety.

TECHNICAL FIELD

The present disclosure relates to capacitance tomography, and more particularly to a speed improvement in the same.

BACKGROUND OF THE INVENTION

Electrical capacitance tomography (ECT) is a technique used to determine the dielectric permittivity distribution in the interior of an object from external capacitance measurements. ECT enables insight into the material distribution within a closed vessel, and consequently, into the governing mechanism in processes occurring within the vessel, without disturbing the processes themselves.

The basic procedure of AC-based capacitance measurement is to apply a sinusoidal voltage signal to an electrode (that forms one plate of a capacitor) and measure the output current/voltage on another electrode (that forms the other plate of the capacitor), from which the capacitance is determined. An existing method, referred to as MECaP (multiple excitation capacitance polling), applies multiple excitation signals to multiple electrodes at each time instance, thereby enabling simultaneous measurement of more than one inter-electrode capacitance from a single receiving electrode. MECaP is limited in that it can only read a single receiving electrode during each step. MECaP increases the measurement speed relative to the traditional single excitation/single receiver system that has been utilized for the past decade. However, in some time-sensitive applications the increased speed is still inadequate for capturing high speed dynamics, which is the intended use of the ECT system.

SUMMARY

In a feature embodiment, a method for operating a sensor includes: simultaneously exciting a first set of electrodes of a plurality of electrodes and sensing an output of each electrode of a second set of electrodes of the plurality of electrodes, storing output data corresponding to the output of each electrode of the second set of electrodes in a memory storage device, shifting at least one electrode from the first set of electrodes to the second set of electrodes and at least one electrode from the second set of electrodes to the first set of electrodes, and repeating the simultaneously exciting and sensing, the storing, and the shifting until an output data has been stored for each possible pair of electrodes in the first and second set of electrodes.

In another embodiment according to the previous embodiment, wherein the first set of electrodes and the second set of electrodes have the same number of electrodes, thereby minimizing a number of iterations of the method.

In another embodiment according to any previous embodiment, wherein the step of simultaneously exciting a first set of electrodes and sensing an output of each electrode of the second set of electrodes includes exciting each electrode in the first set of electrodes with a corresponding unique excitation frequency.

In another embodiment according to any previous embodiment, wherein the step of simultaneously exciting the first set of electrodes and sensing an output of each electrode of the second set of electrodes includes filtering a received signal corresponding to each electrode of the second set of electrodes such that a unique output signal corresponding to each of the unique excitation frequencies is generated for each electrode of the second set of electrodes.

In another embodiment according to any previous embodiment, wherein the step of storing the readings from the second set of electrodes in a memory includes: associating each of the unique output signals with the electrode from the first set having the corresponding excitation frequency and associating each of the unique output signals with the receiving electrode corresponding to the unique output signal, thereby assigning an electrode pair to each of the unique output signals, and storing the assigned electrode pair associated with each of the unique output signals, thereby generating a stored value for each possible pair of electrodes.

Another embodiment according to any previous embodiment, further includes the step of discarding redundant electrode pair sensings prior to storing the unique output signals.

Another embodiment according to any previous embodiment, further includes the step of generating a combined image based on a combination of all of the stored readings.

In another embodiment according to any previous embodiment, wherein the step of simultaneously exciting the first set of electrodes and reading an output of the second set of electrodes further comprises exciting each of the first plurality of electrodes using an AC signal having a frequency unique to the corresponding electrode.

In another feature embodiment, an electrical capacitance tomography (ECT) sensor including: a plurality of electrodes, each configured to operate as an excitation electrode in a first condition and a receiving electrode in a second condition; an electrode control module connected to each of the plurality of electrodes and configured to control a condition of each of the plurality of electrodes; and a plurality of lock-in amplifiers connected to an output of the electrode control module and connected to a data acquisition system of a computer.

In another embodiment according to any previous embodiment, wherein the electrode control module is configured to excite each of the electrodes in the first condition using an excitation frequency unique to that electrode.

In another embodiment according to any previous embodiment, wherein the data acquisition system includes a filter configured to isolate each of the excitation frequencies from a signal received from the lock-in amplifiers.

In another embodiment according to any previous embodiment, wherein the lock-in amplifiers are arranged in a plurality of arrays of lock-in amplifiers.

In another embodiment according to any previous embodiment, wherein the plurality of electrodes is an even number of electrodes.

In another embodiment according to any previous embodiment, wherein the number of electrodes in the first condition is equal to the number of electrodes in the second condition.

In another embodiment according to any previous embodiment, wherein the ECT sensor is an Alternating Current (AC) phase locked ECT detector.

In another feature embodiment, a method for operating a sensor includes: simultaneously exciting a first set of electrodes of a plurality of electrodes and sensing an output of each electrode of a second set of electrodes of said plurality of electrodes, storing output data corresponding to the output of each electrode of the second set of electrodes in a memory storage device, shifting at least one electrode from the first set of electrodes to the second set of electrodes and at least one electrode from the second set of electrodes to the first set of electrodes, and repeating said simultaneously exciting and sensing, said storing, and said shifting.

Another embodiment according to the previous embodiment includes repeating said simultaneously exciting and sensing, said storing, and said shifting until an output data has been stored for each possible pair of electrodes in said plurality of electrodes.

DETAILED DESCRIPTION

Figure 1:
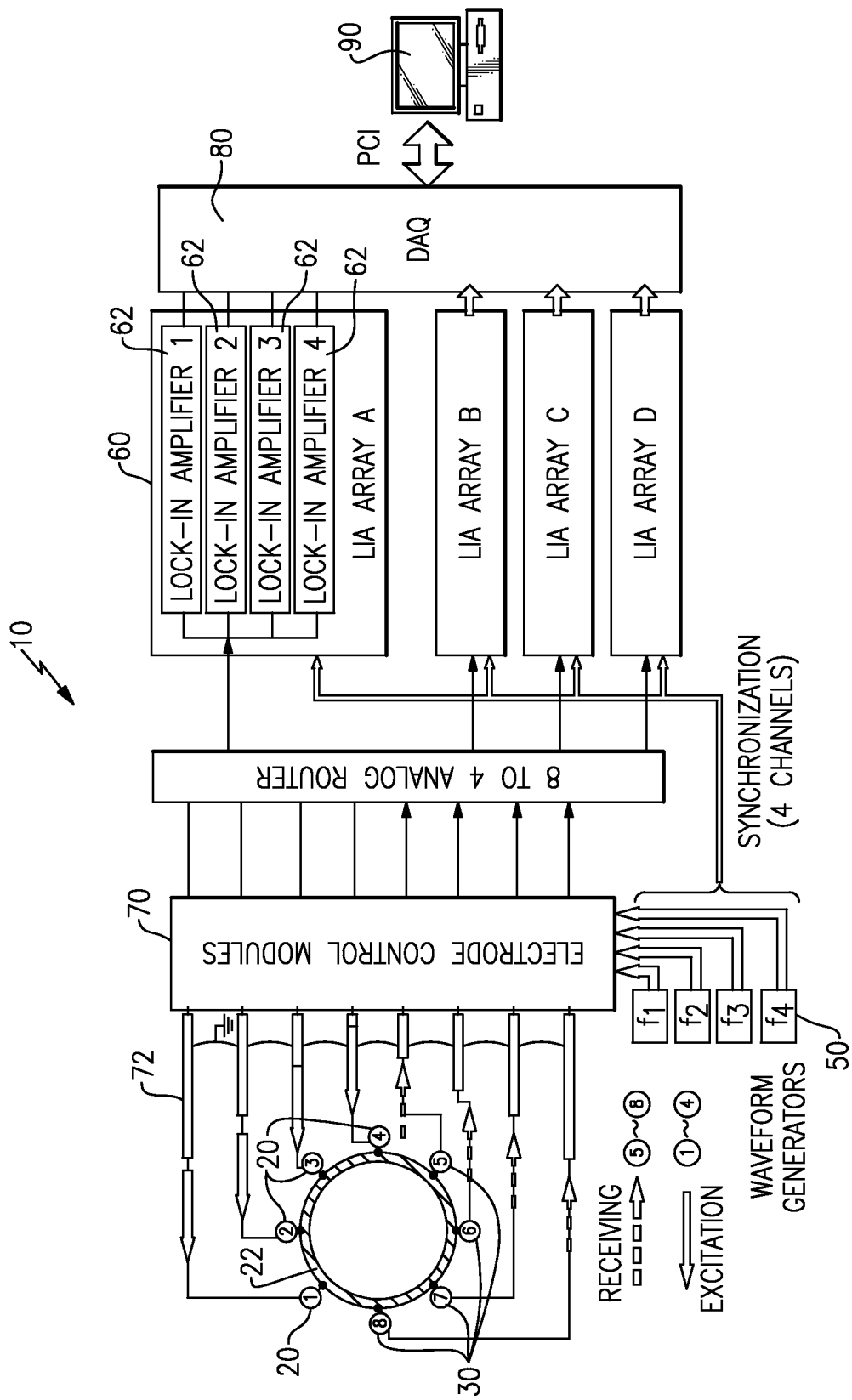
FIG. 1 illustrates an example 8-electrode MEMR circuit.

In order to realize the Multiple-Excitation Multiple-Receiving (MEMR) method described below, an ECT sensor illustrated in FIG. 1 is utilized. The sensor includes multiple electrodes 20, 30 disposed about a sensor ring 22. The electrodes 20, 30 are connected to an electrode control module 70 via standard electrode connections 72. During any given iteration of a sensing step, the electrodes 20, 30 are divided into a first set 20 and a second set 30. The first set 20 is alternately referred to as an excitation set 20, and the second set 30 is alternately referred to as a receiving set 30. The excitation set 20 electrodes each receive a unique frequency from a group of waveform generators 50, through the electrode control module. The electrical connections 72 connecting the receiving set of electrodes 30 receive a resulting output signal from the electrodes 30 in the receiving set. The electrode control module is arranged to control which electrodes 20, 30 are in the first setting (excitation) and which electrodes 20, 30 are in the second setting (receiving) at any given time.

The electrode control module 70 is connected to a group of lock in amplifiers 62 that are arranged in multiple lock in amplifier arrays 60. In this way, the signals received from the receiving electrodes 30 can be sent to a corresponding lock in amplifier 62. A data acquisition component 80 is connected to the lock-in amplifiers 62, and includes multiple filters. The data acquisition amplifier 80 applies the filters to each of the received signals from the lock-in amplifiers and determines a sensor reading for each of the unique excitation frequencies. Thus, an individual reading for each excitation electrode 20 can be isolated from a single receiving electrode 30. In one example, half the electrodes 30 are set to receive at a single time.

The data acquisition component 80 is either connected to, or part of, a computer 90 or computerized control device. Once a reading has been determined for every possible pair of electrodes 20, 30 the computer 90 can combine the readings to generate an ECT map according to known methods, and the computer 90 can respond accordingly.

Described below is the method for improving the measurement speed in Electrical Capacitance Tomography (ECT) using the apparatus illustrated in FIG. 1. The measurement speed is improved by reducing the total number of measurement steps needed to complete each frame (each image). This is achieved through the simultaneous excitation of multiple electrodes and simultaneous receipt of multiple signals (corresponding to capacitance values) in each measurement step, thereby enabling a Multiple-Excitation Multiple-Receiving (MEMR) scheme. Specifically, in an M-electrode ECT sensor 10 (with M being an even integer), the electrodes 20, 30 are divided into a set of excitation electrodes 20 and a group of receiving electrodes 30. In one example, the electrodes 20, 30 are evenly divided into a first set 20 (excitation) and second set 30 (receiving).

Each of the excitation electrodes 20 in the excitation set is excited by a pre-determined frequency, such as $f_1$, $f_2$, $f_{Ne}$. Signals received by the receiving electrodes 30 in the receiving set are separated by a series of lock-in amplifiers 62 arranged in multiple lock in amplifier arrays 60 whose central frequencies are synchronized with a corresponding excitation frequency 50 $f_1$, $f_2$, . . . $f_{Ne}$. Depending on the number of electrodes 20, 30 used in the ECT sensor 10, the technique can increase the frame rate over that of a traditional single excitation-single-receiving (SESR) method, making ECT a high-speed, non-intrusive means for monitoring the dynamics of a fast changing process such as multi-phase flow and flame combustion, with significantly improved time resolution.

MEMR introduces a further improved technique beyond what the MECaP (or MESR, multiple-excitation-single-receiving) method has been able to achieve, by:
1) Further increasing the ECT scanning speed over the traditional AC method and over the AC-based MECaP (MESR) method;
2) Providing a new hardware architecture to enable simultaneous excitation and receiving for the measurement of multiple inter-electrode capacitance values; and
3) Further capitalizing on the use of a frequency selection criterion to avoid interference between channels when multiple excitations are applied to ECT electrodes.

Assume the symbol $N_e$ represents the number of excitation electrodes and $N_r$ represents the number of receiving electrodes 30. In the Multiple-Excitation-Multiple-Receiving (MEMR) scheme, $N_e+N_r=M$, with M representing the total number of electrodes 20, 30. When the number of excitations increases, the number of receiving channels has to decrease, and vice versa. The number of simultaneous capacitance measurements is calculated as the product of $N_e \times N_r$. Using the Lagrangian method, it can be shown that the maximum number of simultaneous capacitance measurements is reached when $N_e$ and $N_r$ satisfy the following relationship: $N_e=N_r=M/2$.

Figure 2:
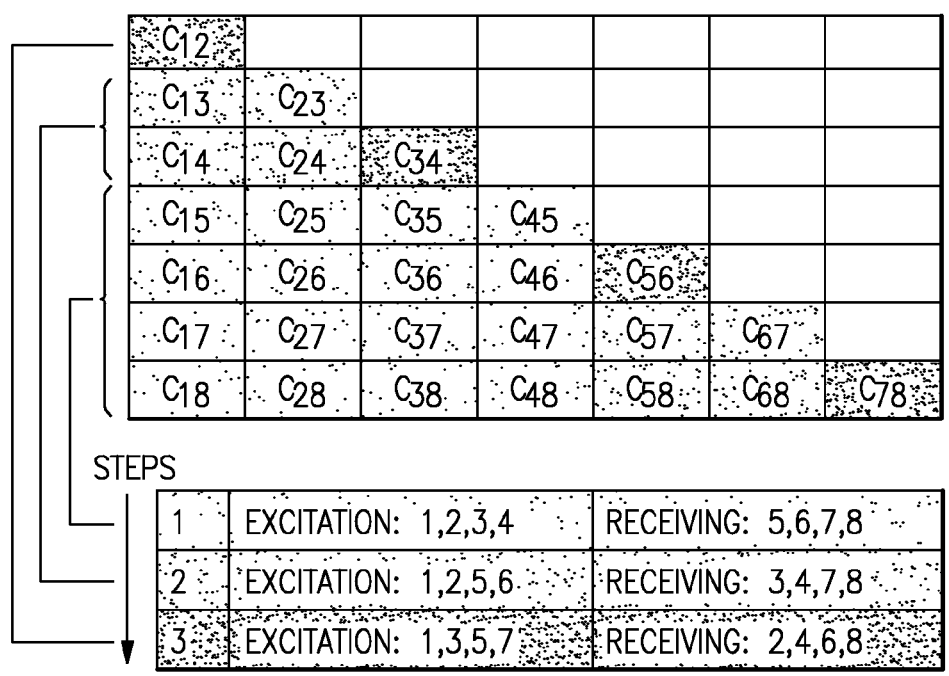
FIG. 2 illustrates an example MEMR control sequence.

Refer now to FIG. 2, which illustrates a MEMR control sequence for a representative case of M=8. With four simultaneous excitations and receiving channels, a maximum of sixteen capacitance values can be measured simultaneously. As a result, all 28 capacitance measurements required for completing a frame in an 8-electrode ECT can be accomplished in three measurement steps. During the first step, electrodes 1, 2, 3 and 4 are in the excitation set of electrodes 20 and electrodes 5, 6, 7 and 8 are in the receiving set of electrodes 30. When transitioning to the second step, electrodes 5 and 6 are shifted from the receiving set of electrodes 30 to the excitation set of electrodes 20 and electrodes 3 and 4 are shifted from the excitation set of electrodes 20 to the receiving set of electrodes 30. Similarly in the transition from the second step to the third step the electrodes 3 and 7 are shifted from the receiving set of electrodes 30 to the excitation set of electrodes 20, and electrodes 2 and 6 are shifted from the excitation set of electrodes 20 to the receiving set of electrodes 30. This shifting is performed by the electrode control module described above with regards to FIG. 1. As can be seen, the electrode control module discards redundant pairings of electrodes, thereby further minimizing the steps required. By way of example, if the electrode control module has already sensed pair C12, any further sensing of pair C12 and C21 is discarded for the current frame, as the pairing has already been sensed. The sensed capacitance values from each step are stored, and are utilized to create the overall image of the frame once all the pairings have been measured.

Comparing this with the traditional ECT where only one capacitance value is measured in each step, the MEMR scheme described herein increases the frame rate by a factor of 9.3. Furthermore, comparing this with the MECaP method of the prior art, the MEMR scheme described herein increases the frame rate by a factor of 2.3.

Figure 3:
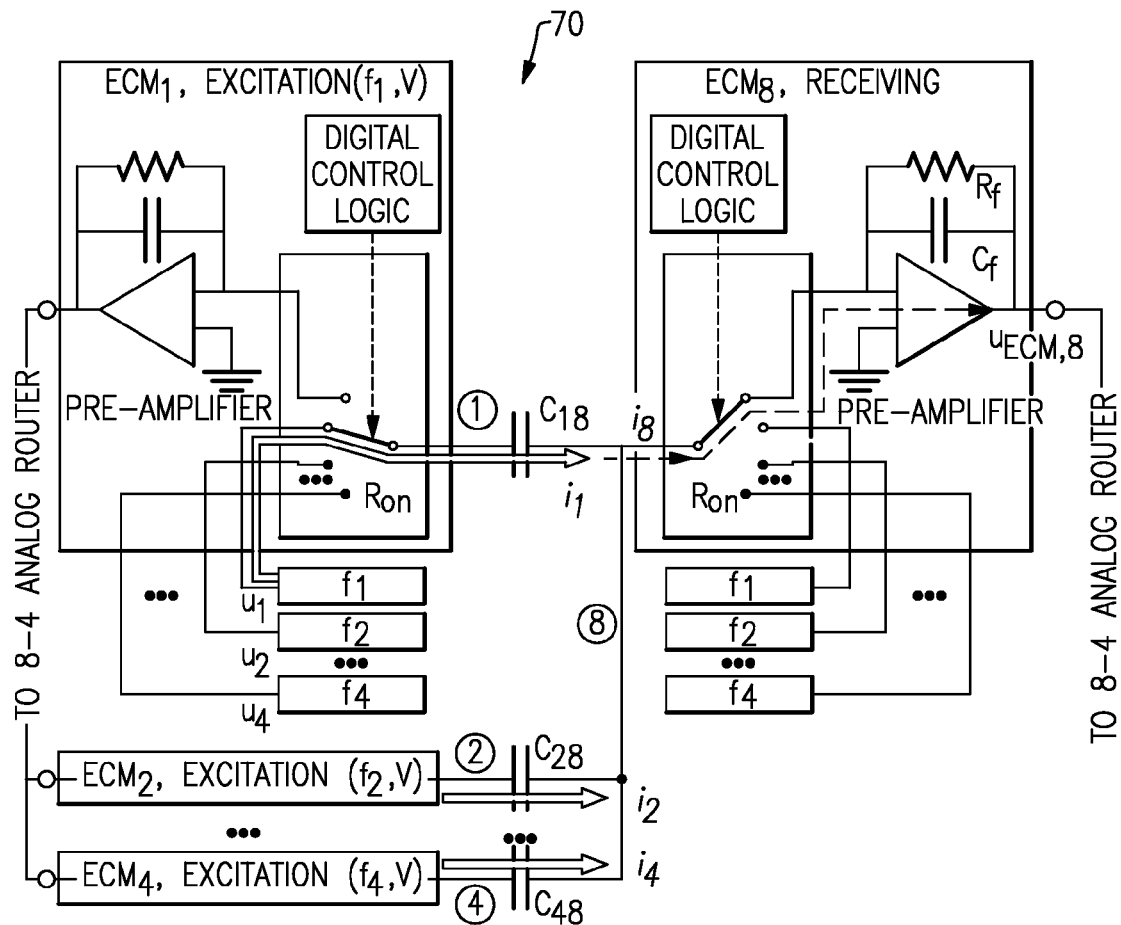
FIG. 3 illustrates an example electrode control module for realizing an MEMR process.

Realization of the MEMR circuit 10 is illustrated using FIG. 1, with four electrodes 20 configured for excitation and four electrodes 30 configured for receiving. A group of Electrode Control Modules 70 (ECM) control the switching of the electrodes 20, 30 to either the excitation or receiving mode, according to the control sequence as shown in FIG. 2. With continued reference to FIGS. 1 and 2, FIG. 3 illustrates an example of electrode control modules (ECM) for realizing an MEMR process where a configuration of eight electrodes (M=8) is controlled, with four excitation and four receiving channels ($N_e$=4), respectively Each of the eight electrodes is controlled by an ECM to connect with either one of the four excitation channels ($f_1$, $f_2$, . . . $f_4$) or the receiving channels through a pre-amplifier and an 8-to-4 analog router circuitry. With this configuration, the ECM enables four excitation signals to be applied to four of the eight electrodes and the receiving channels to be connected with the remaining four electrodes. Based on the Kirchhoff's law, for each of the measurement steps, the relationship between the loop current $i_1$, $i_2$, $i_3$, $i_4$, and $i_8$ and the voltage output of the function generator $u_1$ can be calculated. For a given frequency $\omega=2\pi f_k$ (k=1, 2, . . . 4), the relationship is expressed as shown in equation (1):

$$\begin{bmatrix} -R_{on}-\frac{1}{j\omega C_{18}} & & & & R_{on} \\ & -R_{on}-\frac{1}{j\omega C_{28}} & & & R_{on} \\ & & -R_{on}-\frac{1}{j\omega C_{38}} & & R_{on} \\ & & & -R_{on}-\frac{1}{j\omega C_{48}} & R_{on} \\ 1 & +1 & +1 & +1 & -1 \end{bmatrix} \begin{bmatrix} i_1 \\ i_2 \\ i_3 \\ i_4 \\ i_8 \end{bmatrix} = \begin{bmatrix} u_1 \\ u_1 \\ u_1 \\ u_1 \\ 0 \end{bmatrix} \quad (1)$$

where $R_{on}$ is the resistance of the CMOS switch, and $u_1=V\cdot\sin(2\pi f_1 t)$ is the voltage output from the first waveform generator with frequency $f_1$ and amplitude V. In cases where the impedance of inter-electrode capacitance is much greater than $R_{on}$, it can be derived from Eq. (1) that the currents $i_1 \sim i_4$ are linear functions of the impedances $|1/j\omega C_{18}| \sim |1/j\omega C_{48}|$, respectively.

From the op-amp circuit shown in FIG. 3, the output from the pre-amplifier (j=8) is:

$$u_{ECM,j} = \sum_{i=1\ldots Ne, i\neq j} V_{ECM,ij}\sin(\omega_i t + \varphi_i) \quad (2)$$

Where $V_{ECM, ij}$ is the amplitude of the output AC voltage corresponding to excitation channel #i through the inter-electrode capacitance $C_{ij}$ (j=8 in FIG. 3). By referring to the characteristic of the preamplifier circuit and Equations (1)-(2), the value of $V_{ECM, ij}$ can be expressed as a function of $C_{ij}$, as shown in Equation (3):

$$V_{ECM,ij} = -\left|\frac{j2\pi f_i C_{ij} R_f}{j2\pi f_i C_f R_f + 1}\right| V \quad (3)$$

Where V is the amplitude of the excitation signals, and $R_f$, V and $C_f$ are the feedback resistance and capacitance of the preamplifier, respectively.

For each of the receiving electrodes 30, e.g. electrode #8 (j=8), as shown in FIG. 3, the capacitance $C_{18}$, $C_{28}$, $C_{38}$ and $C_{48}$ are represented by the amplitude $V_{ECM, 18}$, $V_{ECM, 28}$, $V_{ECM, 38}$, and $V_{ECM, 48}$, respectively. An array of Lock-in Amplifiers 60 (LIA), A, B, C, and D, each containing four lock-in amplifiers synchronized with the excitation sources, are designed to extract output AC signal amplitudes and subsequently, calculate the capacitance values according Eq. (2) above. To reduce circuit complexity, an 8-to-4 analog router is employed to bridge the connections between the LIA arrays and the receiving channels. Thus, a total of 16 (4×4) lock-in amplifiers 60 are used in for an 8-eletctrode ECT system.

Figure 4:
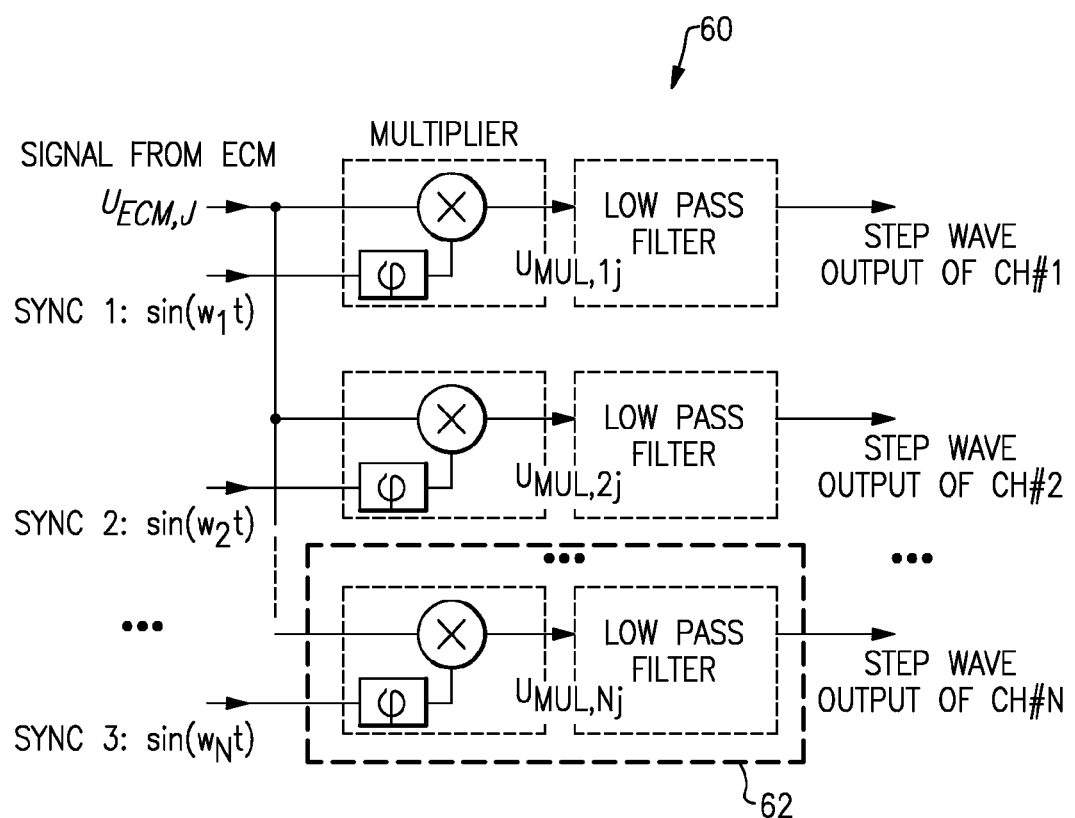
FIG. 4 illustrates an example lock-in-amplifier for the MEMR circuit of FIG. 1.

When the multiple excitation channels are applied, the output signal from each electrode 20, 30 is processed by the ECM 70 according to Eq. (3) and then extracted by the lock-in amplifier (LIA) array 60 to convert the amplitude of a sine wave at each excitation frequency into independent DC voltage levels. FIG. 4 illustrates the configuration of the LIA array 60 containing N individual LIAs 62 to process the signal from ECM 70 #1. By switching the excitation source connected to the electrodes 20, 30 and the connection to ECMs 70 in each measurement step according to FIG. 2, the DC voltage varies proportional to the measured capacitance value according to Eq. (2) and forms a series of step waves with an upper frequency bound being the major angular cutoff frequency $\omega_A$. In each LIA 60, the signal from ECM 70 (selected by the 8-4 analog router) is mixed by the multiplier with the synchronization signal directly coupled from the excitation sources. Assuming that the phase shift (φ) induced by the lock-in amplifier is zero, the output signal from the multiplier corresponding to LIA channel #1 is expressed as shown in equation (4):

$$u_{MUL,1} = \sin(\omega_1 t) \cdot u_{ECM,j} = \sin(\omega_1 t) \cdot \sum_{i=1 \ldots N, i \neq j} V_{ECM,ij} \sin(\omega_i t + \varphi_i) \quad (4)$$

Similarly, the output from the other LIAs is expressed as shown in Equations (5) and (6):

$$u_{MUL,2} = \sin(\omega_2 t) \cdot \sum_{i=1 \ldots N, i \neq j} V_{ECM,ij} \sin(\omega_i t + \varphi_i) \quad (5)$$

$$u_{MUL,N} = \sin(\omega_N t) \cdot \sum_{i=1 \ldots N, i \neq j} V_{ECM,ij} \sin(\omega_i t + \varphi_i) \quad (6)$$

By expanding the right sides of Eq. (4)-(6), it is seen that Eq. (4)-(6) are composed of a series of multiplications of the wave amplitude, $V_{ECM, ij}$, with two sine waves. Each of the multiplications can be expressed in a generalized form as shown in equation (7):

$$V_{ECM,ij} \sin(\omega_i t + \phi_i) \cdot \sin(\omega_n t) = V_{ECM,ij} \cos[(\omega_i - \omega_n)t + \phi_i] - V_{ECM,ij} \cos[(\omega_i + \omega_n)t + \phi_i] (i,j,n=1,2,\ldots N, i \neq j) \quad (7)$$

where the term $\sin(\omega_i t + \phi_i)$ corresponds to the wave components from the excitation source m, and term $\sin(\omega_n)$ corresponds to the synchronization signal being connected to LIA #n. Based on the relationship between the indices i and n, the result of Eq. (7) can be calculated in two cases:

Case 1, i=n: Since $\omega_i = \omega_j = \omega_n$, Equation (7) can be rewritten as equation (8):

$$V_{ECM,ij} \sin(\omega_i t + \phi_i) \cdot \sin(\omega_n t) = V_{ECM,ij} \cos(\phi_i) - V_{ECM,ij} \cos(2\omega_i t + \phi_i) \quad (8)$$

where the first term on the right side is a DC step wave in which each voltage level is determined by the capacitance $C_{ij}$ according to Eq. (2), while the second term $V_{ECM, ij} \cos(2\omega_i t + \phi_i)$ is a high frequency AC cosine wave modulated by the step wave.

Case 2, i≠n: Equation (7) can be rewritten as equation (9):

$$V_{ECM,ij} \sin(\omega_i t + \phi_i) \cdot \sin(\omega_n t) = V_{ECM,ij} \cos[(\omega_i - \omega_n)t + \phi_i] - V_{ECM,ij} \cos[(\omega_i + \omega_n)t + \phi_i] \quad (9)$$

where the first and second term on the right side correspond to a low frequency and high frequency AC wave modulated by the step wave, respectively.

Figure 5:
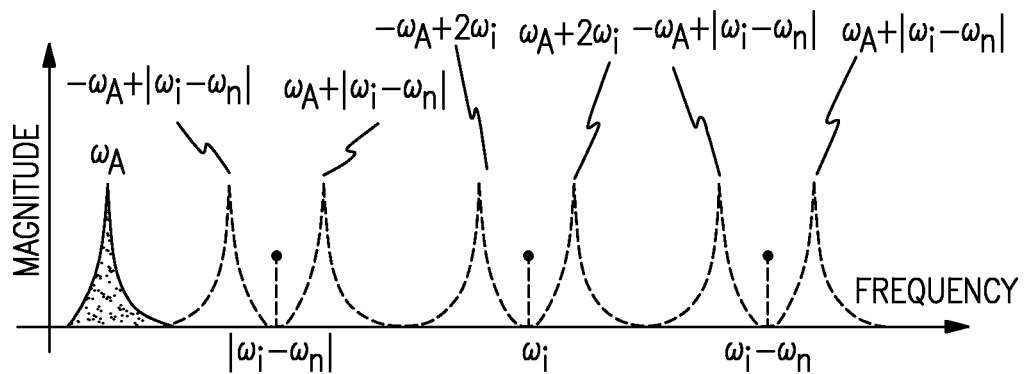
FIG. 5 illustrates a graph of a distribution of frequency components.

By substituting Eq. (8) and (9) in to Eq. (4)-(6), it is seen that in the output signal of each LIA, there is one step wave, together with three step wave modulated cosine waves. The step wave is a signal directly readable by a data acquisition (DAQ) system 80 and then used for the capacitance retrieval. The three step wave modulated cosine waves produce mirrors of the step wave's frequency components (having major angular cutoff frequency $\omega_A$) at each side of the central frequencies, $|\omega_i - \omega_n|$, $\omega_i$, and $(\omega_i + \omega_n)$ as shown in the graph of FIG. 5. For an 8-electrode ECT configuration with a four-excitation-four-receiving arrangement, i=1, 2, 3, 4 and n=1, 2, 3, 4, correspond to the frequency components from the four excitation sources.

In order to enable the low-pass filter to extract only the step wave from the LIA, it is necessary to satisfy the condition that: the lowest mirror frequency component won't overlap with the major frequency component of the step wave. Such a relationship is expressed as shown in equation (10):

$$\min(-\omega_A + |\omega_i - \omega_n|) > \omega_A \; \forall i, n = s1, 2, \ldots N \quad (10)$$

Due to the fact that the frequency components of a step wave are only determined by the measured capacitance value and are independent from the excitation frequencies, Eq (10) can be rewritten as:

$$\min(|\omega_i - \omega_n|) > 2\omega_A \; \forall i, n = 1, 2, \ldots N \quad (11)$$

Figure 6:
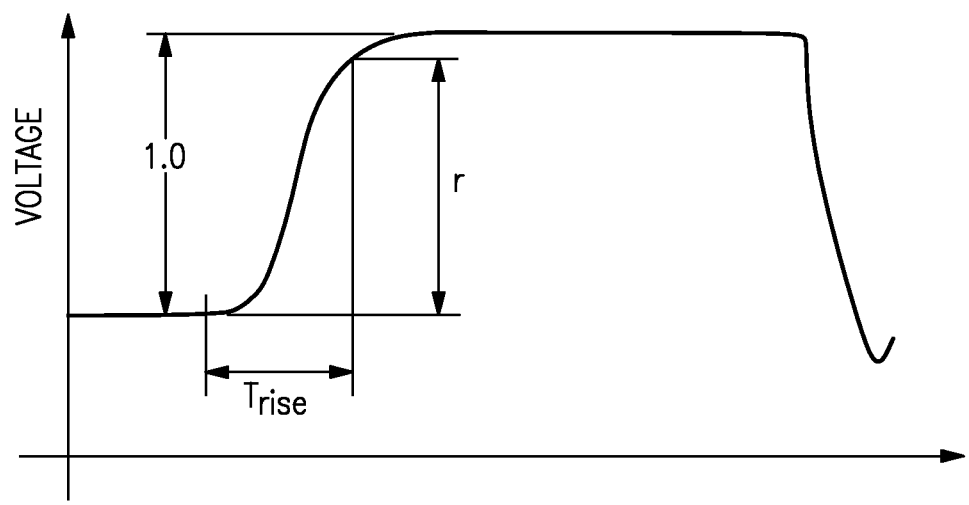
FIG. 6 illustrates a graph of one unit in a step ware.

Practically, the value of $\omega_A$ can be estimated by using the approximation of the cut-off frequency of a step wave (illustrated in FIG. 6), which is expressed as equation (12):

$$\omega_A = \frac{\ln(r) - \ln((1-r))}{T_{rise}} \quad (12)$$

where r and $T_{rise}$ are the amplitude (in percentage) and the corresponding time period of the transient stage (rising-edge). By substituting Eq. (12) into Eq. (11), the necessary condition can be expressed as equation (13):

$$\min(|\omega_i - \omega_n|) > 2\frac{\ln(r) - \ln((1-r))}{T_{rise}} \quad (13)$$

Equation (13) illustrates the fact that, in the MEMR scheme, the minimum difference between any two excitation frequencies must be larger than a threshold determined by the quality of the step wave. Otherwise, the capacitance values measured via multiple excitation sources cannot be successfully separated and calculated from the received signal. As an example, for an ECT system designed to respond to 99% (i.e. r=0.99) of the expected voltage level within 10 μs ($T_{rise}$), as shown in Eq. (13), the corresponding frequency increment between excitation channels must be greater than 146 kHz. In addition, considering the limited band of excitation frequency constrained by the ECT measurement circuitry in practice, Equation (13) also indicates that there is an upper limit on the number of excitation channels required to keep the individual excitation frequencies properly separated from each other.

Figure 7:
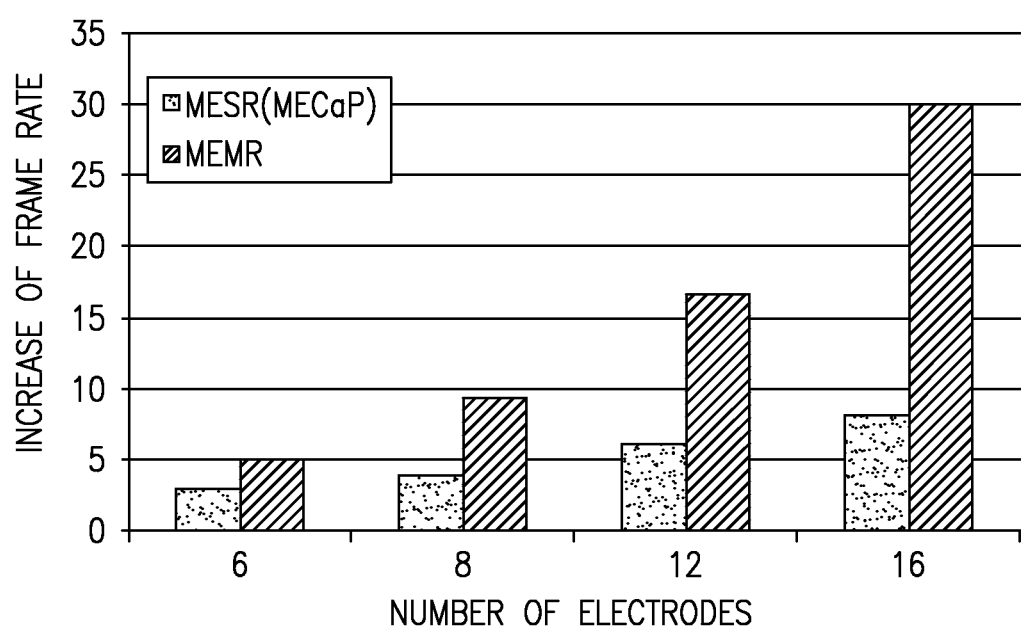
FIG. 7 illustrates a graph of a frame rate improvement enabled by an MEMR method.

As an overview of the frame rate improvement enabled by MEMR and MECaP (MESR) over the traditional single-excitation-single receiving (SESR) method, the total number of measurement steps for completing a frame for an ECT sensor containing 6, 8, 12, and 16 electrodes was calculated. FIG. 7 illustrates the results of this calculation. Compared with the traditional method, the maximum scanning speed increase achieved by MESR is 3 to 8 times, for 6~16 electrodes. The improvement enabled by MEMR, in comparison, is 5 (for 6-electrode) to 30 (for 16 electrode) times speed of the traditional method. Such additional improvement by MEMR is due to the increased number of capacitance measurements in each step, $N_e \times N_r$, which is proportional to the square of M. Thus, when the number of electrodes is increased, MEMR method is able to significantly accelerate the ECT frame scanning speed as compared to MESR methods.

Although an embodiment of this invention has been disclosed, a worker of ordinary skill in this art would recognize that certain modifications would come within the scope of this invention. For that reason, the following claims should be studied to determine the true scope and content of this invention.

The invention claimed is:

1. A method for operating a sensor, comprising:
   simultaneously exciting a first set of electrodes of a plurality of electrodes and sensing an output of each electrode of a second set of electrodes of said plurality of electrodes;
   storing output data corresponding to the output of each electrode of the second set of electrodes in a memory storage device;
   shifting at least one electrode from the first set of electrodes to the second set of electrodes and at least one electrode from the second set of electrodes to the first set of electrodes; and
   repeating said simultaneously exciting and sensing, said storing, and said shifting until an output data has been stored for each possible pair of electrodes in said plurality of electrodes.

2. The method of claim 1, wherein the first set of electrodes and the second set of electrodes have the same number of electrodes, thereby minimizing a number of iterations of the method.

3. The method of claim 1, wherein the step of simultaneously exciting a first set of electrodes and sensing an output of each electrode of the second set of electrodes includes exciting each electrode in the first set of electrodes with a corresponding unique excitation frequency.

4. The method of claim 3, wherein the step of simultaneously exciting the first set of electrodes and sensing an output of each electrode of the second set of electrodes includes filtering a received signal corresponding to each electrode of the second set of electrodes such that a unique output signal corresponding to each of the unique excitation frequencies is generated for each electrode of the second set of electrodes.

5. The method of claim 4, wherein the step of storing the readings from the second set of electrodes in a memory comprises:
   associating each of the unique output signals with the electrode from the first set having the corresponding excitation frequency and associating each of the unique output signals with the receiving electrode corresponding to the unique output signal, thereby assigning an electrode pair to each of the unique output signals; and
   storing the assigned electrode pair associated with each of the unique output signals, thereby generating a stored value for each possible pair of electrodes.

6. The method of claim 5, further comprising the step of discarding redundant electrode pair sensings prior to storing the unique output signals.

7. The method of claim 1 further comprising the step of generating a combined image based on a combination of all of the stored readings.

8. The method of claim 1, wherein the step of simultaneously exciting the first set of electrodes and reading an output of the second set of electrodes further comprises exciting each of the first plurality of electrodes using an AC signal having a frequency unique to the corresponding electrode.

9. A method for operating a sensor, comprising:
   simultaneously exciting a first set of electrodes of a plurality of electrodes and sensing an output of each electrode of a second set of electrodes of said plurality of electrodes;
   storing output data corresponding to the output of each electrode of the second set of electrodes in a memory storage device;
   shifting at least one electrode from the first set of electrodes to the second set of electrodes and at least one electrode from the second set of electrodes to the first set of electrodes; and
   repeating said simultaneously exciting and sensing, said storing, and said shifting.

10. The method of claim 9, further comprising repeating said simultaneously exciting and sensing, said storing, and said shifting until an output data has been stored for each possible pair of electrodes in said plurality of electrodes.

* * * * *

UNITED STATES PATENT AND TRADEMARK OFFICE
CERTIFICATE OF CORRECTION

PATENT NO. : 9,581,560 B2  Page 1 of 1
APPLICATION NO. : 14/813925
DATED : February 28, 2017
INVENTOR(S) : Zhaoyan Fan et al.

It is certified that error appears in the above-identified patent and that said Letters Patent is hereby corrected as shown below:

In the Claims

In Claim 7, Column 10, Line 15; after "stored" replace "readings" with --output data--

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*